United States Patent [19]

Toukan et al.

[11] 4,343,946

[45] Aug. 10, 1982

[54] PURIFICATION OF 2-MERCAPTOBENZOTHIAZOLE

[75] Inventors: Sameeh S. Toukan, Phoenixville; Piero Nannelli, King of Prussia, both of Pa.

[73] Assignee: Pennwalt Corporation, Philadelphia, Pa.

[21] Appl. No.: 161,824

[22] Filed: Jun. 23, 1980

[51] Int. Cl.³ .................................................. C07D 277/72
[52] U.S. Cl. ..................................... 548/177; 548/176
[58] Field of Search ......................... 548/165, 176, 177

[56] References Cited

U.S. PATENT DOCUMENTS

| | | | |
|---|---|---|---|
| 2,117,120 | 5/1938 | Smith et al. | 548/177 |
| 2,137,820 | 11/1938 | Williams et al. | 548/165 |
| 2,631,153 | 3/1953 | Paul et al. | 548/177 |
| 2,730,528 | 1/1956 | Weyker et al. | 548/177 |

FOREIGN PATENT DOCUMENTS 41-10108  5/1966  Japan ............................. 548/165

*Primary Examiner*—David B. Springer
*Attorney, Agent, or Firm*—John S. Munday

[57] ABSTRACT

A process for the purification of crude 2-mercaptobenzothiazole, prepared by reacting aniline, carbon disulfide and sulfur at elevated temperature and pressure is described. The process comprises the reaction of crude 2-mercaptobenzothiazole with 5-20%, preferably 10-12%, molar excess aqueous alkali metal hydroxide having a concentration of 3 to 20% by weight alkali metal hydroxide at 70° to 90° C. for 0.5-4 hours, with vigorous agitation, followed by filtration of the insoluble impurities and acidification of the filtrate with a non-oxidizing mineral acid, such as hydrochloric and sulfuric acids. The precipitated, filtered product is washed with water and collected in 98-100% yield and 95-98.5% purity.

4 Claims, No Drawings

PURIFICATION OF 2-MERCAPTOBENZOTHIAZOLE

BACKGROUND OF THE INVENTION

2-Mercaptobenzothiazole, and its derivatives, are commercially important in the rubber industry as vulcanization accelerators. Many patents and literature references have been published on the preparation and purification of 2-mercaptobenzothiazole.

One of the methods of purification is the treatment of 2-mercaptobenzothiazole with carbon disulfide, according to U.S. Pat. No. 2,090,233 and U.S. Pat. No. 4,061,046. The former requires several extractions of crude 2-mercaptobenzothiazole with carbon disulfide in order to remove impurities (tars) and by-products such as benzothiazole, diphenylthiourea, etc., while U.S. Pat. No. 4,061,646 requires treatment of the molten (about 200° C.) crude 2-mercaptobenzothiazole with cold carbon disulfide by liquid—liquid extraction, thereby forming a slurry of 2-mercaptobenzothiazole crystals which are then filtered and dried. Considerable time and equipment are required to process the resulting carbon disulfides extract containing impurities, unreacted starting materials, and reusable by-products. Moreover, carbon disulfide is a health hazard and is extremely flammable. Another method of purification as disclosed by U.S. Pat. No. 3,681,371, requires the distillation of the crude molten 2-mercaptobenzothiazole, followed by treatment of the distillate with sodium hydroxide. Yet, another patent, U.S. Pat. No. 2,631,153, teaches an improved method for purifying 2-mercaptobenzothiazole involving its treatment with aqueous alkali, aeration of the alkaline solution, and precipitation with an acid, to obtain a high-purity product. In both of the above-mentioned procedures, the time and apparatus required to carry out the distillation and aeration make the processes costly, time-consuming, and difficult to perform on an individual scale.

In a similar process, U.S. Pat. No. 3,804,846, discloses the purification of crude 2-mercaptobenzothiazole by reaction of an alkaline aqueous solution of 2-mercaptobenzothiazole with an oxidizing agent such as hydrogen peroxide, while air is passed through the alkaline solution at 70° C., and the resulting oxidation products are coagulated on activated carbon, thereby removing the impurities. The above-mentioned disadvantages apply to this process as well, in addition to the fact that as a result of excessive oxidation, the disulfide by-product (2,2'-dithio-bisbenzothiazole) is formed, resulting in less pure 2-mercaptobenzothiazole product.

Other procedures, such as disclosed in U.S. Pat. No. 3,770,759 and U.S. Pat. No. 3,904,638, require the use of organic solvents such as toluene and xylene. In all of these processes, additional equipment and longer time are needed to carry out the purification, while the hazard of toxic gases and fire make them unnecessarily expensive and a menace to the safety of the operators.

BRIEF DESCRIPTION OF THE INVENTION

We have now discovered a simple and economical process for the purification of crude 2-mercaptobenzothiazole in high yield and high purity. The process of the invention comprises five essential steps:

1. Treatment of the crude molten 2-mercaptobenzothiazole with a molar excess of aqueous alkali metal hydroxide solution at 70°-90° C. for 0.5-4 hours, 2. Separation of solid impurities from the aqueous solution of the alkali metal hydroxide as by filtration, for example, 3. Acidification of the filtrate with an excess of aqueous non-oxidizing mineral acid solution to precipitate 2-mercaptobenzothiazole, 4. Separating the precipitated 2-mercaptobenzothiazole and washing the separated 2-mercaptobenzothiazole with water, and 5. Drying the 2-mercaptobenzothiazole.

The purified 2-mercaptobenzothiazole has a melting point range of 172°-176° C. and a purity of 95 to 98.5%. The process affords a 98-100% yield based on the recoverable amount of 2-mercaptobenzothiazole in the crude product.

DETAILED DESCRIPTION OF THE INVENTION

In carrying out the process of our invention, the crude molten 2-mercaptobenzothiazole (generally assaying 80-85% 2-mercaptobenzothiazole) obtained by reaction of aniline, carbon disulfide and sulfur at high temperature and elevated pressure is treated with dilute aqueous alkali metal hydroxide solution with vigorous stirring. The molar excess of alkali metal hydroxide used is in the range of 5-20%, preferably 10-12%, based on the content of pure 2-mercaptobenzothiazole in the crude. Examples of the alkali metal hydroxides are sodium hydroxide and potassium hydroxide. The concentration of the alkali metal hydroxide solution is 3-20% by weight and preferably 5-8%. Preferably, the crude molten 2-mercaptobenzothiazole is discharged into the aqueous alkali metal hydroxide solution.

After treatment of the crude 2-mercaptobenzothiazole with alkali metal hydroxide is completed, the mixture is heated with vigorous stirring at 70°-90° C., preferably at 75°-80° C., for 0.5-4 hours, followed by separation of the liquid from undissolved impurities, preferably by filtration. The separated solid impurities can be washed with water. Surprisingly, almost all of the 2-mercaptobenzothiazole is dissolved as the alkali metal salt, while most of the impurities remain insoluble in the form of a dark sticky cake. This is contrary to the teaching of U.S. Pat. No. 3,681,371 (Col. 5, Line 20), where a solubilizing temperature of 25°-35° C. is recommended. The advantage of using higher temperature and excess alkali is probably due to their effect of diminishing the tendency of the impurities to form colloidal solution when in contact with the alkali metal hydroxide, so that when the alkaline filtrate is acidified, a smaller amount of impurities co-precipitates with the purified 2-mercaptobenzothiazole. However, if the temperature is too high, it will partially split the thiazole ring, resulting in less pure product and lower yield.

The insoluble filter cake, containing the impurities, is usually a very dark, slightly soft, sticky mass which amounts to approximately 5-10% of the original weight of the crude 2-mercaptobenzothiazole. It contains less than 10% of unreacted 2-mercaptobenzothiazole. It can be processed further and most of its content of 2-mercaptobenzothiazole can be recovered. The rest of the filter cake is composed of by-products and intermediates such as benzothiazole, anilinobenzothiazole, 2,2'-dithio-bisbenzothiazole, diphenylthiourea, phenylisothiocyanate, unreacted sulfur and aniline and a resinous tar unknown in composition and chemical structure.

Aeration of the alkaline red filtrate (U.S. Pat. No. 2,631,153) surprisingly does not afford a purer product.

More surprisingly, filtration of the alkaline solution, while hot, i.e. at temperatures above 50° C. results in a product approximately equal in purity to the product obtained when filtration is done at room temperature and the recovery of the purified 2-mercaptobenzothiazole from the crude is increased.

Acidification of the filtrate to precipitate the purified 2-mercaptobenzothiazole is carried out by treating the dark red filtrate with a non-oxidizing aqueous mineral acid solution. The rate of addition of the alkali metal salt of 2-mercaptobenzothiazole to the mineral acid is limited by the temperature of the mixture, which must remain below about 35° C. The molar ratio of pure 2-mercaptobenzothiazole (content of pure product in the crude is determined by analysis) to hydrochloric acid is in the range of 1:1.1 to 1:1.2. Suitable non-oxidizing mineral acids are sulfuric acid, phosphoric acid, and hydrochloric acid. The order of addition can be reversed, but it is preferable that the alkaline filtrate be added to the acid solution. Concentration of the aqueous mineral acid solution can be within the range of 5-30% by weight of acid.

The precipitated and purified 2-mercaptobenzothiazole is separated from the acid solution by filtering, decantation or centrifuging, and the separated pale yellow solid is washed several times with water to remove residual acid, until the last washing is close to a pH of 7. Air drying, followed by vacuum drying, at about 60° C., affords 98-100% yield (based on recoverable amount of 2-mercaptobenzothiazole in crude) of a pale yellow solid having a melting point of 172°-176° C. and a purity of 95-98.5%.

As previously stated the treatment of crude 2-mercaptobenzothiazole, in accord with the present invention, offers many advantages over prior art processes. Of particular advantage is that the amount of unrecovered 2-mercaptobenzothiazole present in the alkali insoluble fraction is reduced significantly, thereby increasing the yield (98-100%).

The amount of waste material (alkali-insoluble solids) either to be disposed of or to be treated to recover additional 2-mercaptobenzothiazole is consequently greatly reduced, indicating a more efficient extraction, and only simple, inexpensive equipment, such as mixing vessels and filter presses are needed to prepare 2-mercaptobenzothiazole.

The best mode of practising our invention will be apparent from a consideration of the following examples:

EXAMPLE 1 a. One-hundred and forty grams of crude molten 2-mercaptobenzothiazole (2-mercaptobenzole, 85% pure—0.70 mole), prepared by a continuous process from aniline, sulfur and carbon disulfide, was added to a vigorously stirred, hot 4.7% aqueous sodium hydroxide solution (664 g, 0.77 mole of NaOH; 10% excess), at about 50° C. As a result, the temperature of the mixture rose to 60° C. The vigorously stirred, hot reaction mixture was heated at 75°-80° C. for 4 hours. The reaction mixture contained three spherical masses which were removed by decantation. The decanted liquid was aerated for 2 hours by bubbling air through the solution at about 60° C., at the rate of 1.0 liter of air per minute. After 1¾ hours from the time the aeration started, the color of the solution changed from dark red to orange yellow, which lasted only a few minutes before the color changed back to dark red. About half of the aerated hot solution was filtered while hot (Part B, temperature about 51° C.), while the other half was allowed to cool to room temperature before filtering (Part A). The total amount of the dried insoluble material, including the solid collected as a result of decantation, weighed 12.05 g (8.6% of the weight of the crude) and contained 9.5% of unrecovered 2-mercaptobenzothiazole.

Each filtrate was added drop-wise (fast addition) to a well-stirred 6% w/v hydrochloric acid (310 ml.). The temperature was kept below 35° C. during the addition period. The pH of the acidified mixture was about 1. Stirring was continued for about 15 minutes before the precipitated light yellow solid was filtered off. It was then washed several times with water until the last washing was close to neutral. Vacuum drying at about 60° C. afforded a total of 114.0 g of a light yellow solid, m.p. 169°-175° C.

Analysis Part A: 96.9% pure (filtered cold).
Analysis Part B: 96.7% pure (filtered hot).

b. The experiment was repeated using same quantities and procedure, except that no aeration was performed. The decanted liquid was divided into two parts: A and B. Part A was filtered at room temperature, while Part B was filtered at about 60° C. A total of 120.8 g of a light yellow solid was obtained, m.p. 169°-174° C.

Analysis Part A: 97.3% pure (filtered cold).
Analysis Part B: 97.1% pure (filtered hot).

The total yield for both experiments, A and B, was 98.6% (based on the content of 2-mercaptobenzothiazole crude).

EXAMPLE 2

By following the procedure of Example 1(b), 194.5 g (1 mole) of crude solid 2-mercaptobenzothiazole (86% pure) was treated with 936 g of 4.7% sodium hydroxide aqueous solution (1.1 mole of NaOH, 10% excess). There was obtained a total of 173 g (100% yield) of a pale yellow solid, m.p. 172°-177° C. The weight of the insoluble cake was only 10.0 g (5.1% of the weight of crude) and contained 16.1% of unreacted 2-mercaptobenzothiazole.

Analysis Part A: 98.5% pure (filtered cold).
Analysis Part B: 98.1% pure (filtered hot).

EXAMPLE 3

(Using only 5% molar excess of 4.7% sodium hydroxide at 75°-80° C.).

Two-hundred and twenty-four grams (1.05 mole) of crude molten 2-mercaptobenzothiazole (78.0% pure) were added to a vigorously stirred 4.7% aqueous sodium hydroxide solution (936 g, 1.1 mole of NaOH, 5% excess) at room temperature. The resulting dark brown mixture was heated at 75°-80° C. for three hours. The dark, soft, sticky insoluble material (15.5% of the weight of the crude) was filtered off, washed several times with water, then vacuum dried at about 40° C. to weight 34.8 g. The dark red filtrate was acidified with hydrochloric acid as described in Example 1(a), to obtain 172.7 g (98.6% yield) of a light yellow solid, m.p. 169°-175° C.

Analysis—96.9% pure.

EXAMPLE 4

(Using 10% molar excess of 20% NaOH at 75°-80° C.).

Two hundred and fifteen grams (1.005 mole) of molten crude MBT (78.0% pure), prepared by a continuous process from aniline, sulfur, and carbon disulfide, was added to a vigorously stirred 20% aqueous sodium hydroxide solution (220 g, 1.1 mole; 9.5% excess) at room temperature. As a result, the temperature of the stirred mixture rose to 63° C. The mixture was then heated to 75° C. and maintained at 75°–80° C. range for one half hour. The reaction mixture was diluted with 760 ml of distilled water, then heated back to 75° C. for 5–10 minutes before it was divided into approximately two equal parts (about 500 ml each). Part A was allowed to cool to room temperature before filtration while Part B was filtered hot (about 75° C.). Combined weight of the filtered insoluble material was 24.0 g (11.1% of the weight of the crude).

The filtered Part B was treated with 450 ml of 6% w/v hydrochloric acid (excess) and processed as in Example 1(a) to obtain 92.1 g of a light yellow solid; m. p. 171°–175° C. Part A was further sub-divided into: Part C measuring 300 ml and Part D measuring 220 ml.

Part C was treated with 225 ml of 6% w/v HCl aqueous solution (excess) as in Example 1(a). The pH of the acidified mixture was about 1. There was obtained 50.2 g of a light yellow solid, m. p. 171°–174° C.

Part D was treated with 125 ml of 6% w/v HCl solution, then the pH of the resulting mixture was adjusted to 7. There was obtained 34.5 g of a light yellow solid, m. p. 168°–173° C. Total yield of all three fractions was 176.8 g (100%).

Analysis Part B: 95.2% pure (filtered hot).

Analysis Part C: 95.6% pure (filtered cold and acidified to pH 1).

Analysis Part D: 95.0% pure (filtered cold and pH adjusted to 7).

EXAMPLE 5

(Effect of low temperature and using 7% molar excess of 4.7% NaOH at 50°–60° C.).

Reaction of MBT (78% pure), prepared by a continuous process from aniline, sulfur, and carbon disulfide, with sodium hydroxide in approximately 1:1.07 molar ratio at 50°–60° C. for 2.5 hours and aeration of half of the filtered reaction mixture afforded two grades of product: The aerated grade was 94.0% pure while the non-aerated was 95.8% pure. The weight of the insoluble cake containing the impurities and unreacted MBT was equivalent to 17.3% of the original weight of the crude and contained 42.2% of unreacted MBT.

We claim:

1. In a process for purifying crude molten 2-mercaptobenzothiazole, prepared by reacting aniline carbon disulfide and sulfur at elevated temperature and pressure, in which the purification includes the steps of separating dissolved alkali metal salt of 2-mercaptobenzothiazole from undissolved impurities, treating the dissolved alkali metal salt of 2-mercaptobenzothiazole with an excess of a non-oxidizing mineral acid to precipitate a slurry of purified 2-mercaptobenzothiazole, separating the purified 2-mercaptobenzothiazole solids from the slurry to obtain 2-mercaptobenzothiazole solids, washing the solids with water, and drying the purified 2-mercaptobenzothiazole, the improvement comprising; forming said dissolved alkali metal salt at 2-mercaptobenzothiazole and said dissolved impurities by the steps of slowly adding crude molten 2-mercaptobenzothiazole into an aqueous alkali metal hydroxide solution, using vigorous agitation, said alkali hydroxide being at a concentration of about 3 to 20 percent by weight alkali metal hydroxide and the amount of alkali metal hydroxide being at about 5 to 20 percent molar excess based upon the content of the pure 2-mercaptobenzothiazole in the crude molten 2-mercaptobenzothiazole; and heating, while agitating, the mixture of said crude molten 2-mercaptobenzothiazole and aqueous alkali metal hydroxide solution at a temperature of about 70° to 90° C. for about 0.5 to 4 hours to dissolve the 2-mercaptobenzothiazole as the alkali metal salt.

2. The process of claim 1 in which the alkali metal hydroxide is sodium hydroxide.

3. The process of claim 1 in which the concentration of the alkali metal hydroxide solution is within the range of 5 to 8% by weight.

4. The process of claim 1 in which the molar excess of alkali metal hydroxide is within the range of 10 to 12%.

* * * * *